United States Patent [19]

Kraska

[11] 4,255,426
[45] Mar. 10, 1981

[54] 1-(2-HYDROXY-3-N-ALKOXYPROPYL)-4-SUBSTITUTED-PIPERAZINES AND PIPERIDINES

[75] Inventor: Allen R. Kraska, East Lyme, Conn.

[73] Assignee: Pfizer Inc., New York, N.Y.

[21] Appl. No.: 55,936

[22] Filed: Jul. 9, 1979

[51] Int. Cl.³ .................. A61K 31/495; C07D 295/08
[52] U.S. Cl. ................................... 424/250; 544/394; 544/401
[58] Field of Search ................. 544/401, 394; 424/250

[56] References Cited

U.S. PATENT DOCUMENTS

| | | | |
|---|---|---|---|
| 3,051,709 | 8/1962 | Shapiro et al. | 544/401 |
| 3,624,082 | 11/1971 | Lewis et al. | 544/401 |
| 3,668,206 | 6/1972 | Narayanan et al. | 544/401 |
| 3,935,267 | 1/1976 | Hauck et al. | 544/401 |
| 3,947,446 | 3/1976 | Witte et al. | 544/401 |
| 3,968,218 | 7/1976 | Bouillon et al. | 544/401 |
| 4,093,631 | 6/1978 | Gardner | 544/401 |
| 4,166,132 | 8/1979 | Kraska | 424/330 |
| 4,173,641 | 11/1979 | Kraska | 424/267 |

*Primary Examiner*—Jose Tovar
*Attorney, Agent, or Firm*—Francis X. Murphy; Charles J. Knuth; Peter C. Richardson

[57] ABSTRACT

1-(2-Hydroxy-3-n-alkoxypropyl)-4-substituted-piperazines and piperidines and derivatives thereof useful as immune regulants are disclosed. Also disclosed are pharmaceutical compositions containing the novel compounds and a method of regulating the immune response of a subject by administration of the novel compounds.

21 Claims, No Drawings

1-(2-HYDROXY-3-N-ALKOXYPROPYL)-4-SUBSTITUTED-PIPERAZINES AND PIPERIDINES

BACKGROUND OF THE INVENTION

This invention relates to novel 1-(2-hydroxy-3-n-alkoxypropyl)-4-substituted-piperazines and piperidines useful as immune regulants.

A number of compounds have been known in the art to be useful as antiinflammatory agents, for example the corticosteriods, phenylbutazone, indomethacin and various 3,4-dihydro-4-oxo-2H-1,2-benzothiazine-4-carboxamide-1,1-dioxides, such as those disclosed in U.S. Pat. No. 3,591,584. Accordingly, these compounds have been of therapeutic value in the treatment of arthritic and other inflammatory conditions such as rheumatoid arthritis. Such conditions have also been treated by administration of immunoregulatory agents, such as levamisole, as described for example in Arthritis Rheumatism, 20 1445 (1977) and Lancet, 1, 393 (1976).

It is also known that biological vaccines such as *Corynebacterium pavrum* and BCG, a viable strain of *Mycobacterium bovis*, have utility as immune stimulants of the reticulo-endothelial system and are thereby capable of increasing the resistance of a warm-blooded animal to tumors. However, the use of these agents has been restricted by hepatic-renal toxicity, granuloma formation, neutropenia and inconsistent therapeutic effects. Accordingly, it has been of continuing interest to develop non-biological, systemically active immune stimulants for use in increasing the resistance of a host to tumors. For discussions of the stimulation of cell-mediated immunity and antitumoral activity, see Herberman, Ad. Cancer Res., 19, 207 (1971), Jordan and Merigan, Ann. Rev. Pharmacol., 15, 157 (1975), Levy and Wheelock, Adv. Cancer Res., 20, 131 (1972) and Sinkovics, Post Graduate Medicine, 59, 110 (1976).

SUMMARY OF THE INVENTION

The present invention relates to novel 1-(2-hydroxy-3-n-alkoxypropyl)-4-substituted-piperazines and piperidines having immune regulant activity. More specifically, the compounds of the present invention are those of Formula I:

$$R_1-O-CH_2-CH-CH_2-X \quad \text{I}$$
$$\phantom{R_1-O-CH_2-}\overset{|}{\phantom{C}}\phantom{H-CH_2-X}$$
$$\phantom{R_1-O-CH_2-}OH$$

and the pharmaceutically acceptable acid addition salts thereof, wherein $R_1$ is n-alkyl of 10 to 20 carbon atoms; and X is selected from the group consisting of:

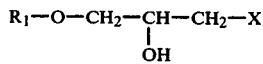

wherein $R_2$ is selected from the group consisting of hydrogen, alkyl of 1 to 3 carbon atoms, benzyl, monosubstituted benzyl, phenyl and monosubstituted phenyl, wherein said substituents are selected from the group consisting of chloro, bromo, fluoro, alkyl of 1 to 3 carbon atoms, alkoxy of 1 to 3 carbon atoms and trifluoromethyl; $R_3$ is selected from the group consisting of hydrogen, methyl, $-CH_2NH_2$ and $-CONH_2$.

One group of compounds of interest is that wherein X is $R_2$-substituted-piperazino. Preferred compounds are those wherein $R_1$ is from 16 to 20 carbon atoms, most preferably 16 or 18 carbon atoms. Preferred substituents for $R_2$ are benzyl and monosubstituted benzyl, for example 4-chlorobenzyl, 4-fluorobenzyl, 4-methylbenzyl, 4-methoxybenzyl, phenyl and monosubstituted phenyl for example 3-trifluoromethylphenyl. An especially preferred group for $R_2$ is benzyl.

A further group of compounds of interest is that wherein X is ($R_2$, $R_3$)-substituted-piperidino. Preferred compounds are those wherein $R_1$ is of 16 to 20 carbon atoms, most preferably 16 or 18 carbon atoms. Preferred substituents for $R_2$ are hydrogen and phenyl, including those compounds wherein $R_3$ is either hydrogen, methyl, or $-CH_2NH_2$ or $-CONH_2$.

The present invention also includes pharmaceutical compositions containing the novel compounds of formula I together with a pharmaceutically-acceptable carrier or diluent. Preferred pharmaceutical compositions are those containing the preferred novel compounds of formula I as set forth hereinabove.

Also embraced by the present invention is a method of immune regulation in a host which comprises administering to the host an effective immune regulant amount of a compound of formula I, preferably selected from the preferred compounds of formula I described hereinabove.

DETAILED DESCRIPTION OF THE INVENTION

The novel compounds of formula I are readily prepared by reaction of an appropriate 2,3-epoxypropyl-n-alkyl ether with a suitable substituted piperidine or piperazine. The 2,3-epoxypropyl-n-alkyl ether is prepared by reaction of an n-alkyl alcohol with an allyl halide, preferably allyl chloride or bromide. The reaction is generally conducted in the presence of an alkali metal hydride such as sodium hydride in an inert organic solvent, such as dimethyl formamide, at temperatures from about 50° C. to 120° C., preferably 75°–100° C. The allyl-n-alkyl ether formed in this reaction is then oxidized to the corresponding 2,3-epoxypropyl-n-alkyl ether by conventional methods using, for example, a peroxy acid as the oxidizing agent, for example, perbenzoic, acid, m-chloro-perbenzoic acid and the like. The reaction is generally conducted in an inert organic solvent, such as methylene chloride, chloroform, and the like at a temperature of about 10°–50° C., preferably at about room temperature.

The 2,3-epoxypropyl-n-alkyl ether is reacted with an appropriate 1-$R_2$-substituted-piperazine or a 4,4-$R_2R_3$-substituted-piperidine. The reaction is effected by heating the reactants at a temperature of about 75° C. to about 250° C., preferably at about 150° to 200° C., preferably employing a small excess of the substituted piperazine or piperidine. The time necessary for completion of the reaction will vary with the temperature employed but is generally from about 15 minutes to about 2 hours at the preferred temperatures in the range 150° to 200° C. The reaction is preferably conducted without the addition of a solvent, but is desired, a reaction inert solvent, such as dimethyl formamide and the like, may be employed.

For preparation of the $R_2$-substituted-piperazino compounds of this invention an alternative and convenient method of preparation is to react the 2,3-epoxypropyl-n-alkyl ether with the readily available 1-benzyl-piperazine to form 1-benzyl-4-(2-hydroxy-3-n-alkoxypropyl)-piperazine, in accord with the reaction procedures described above. The 1-benzyl group may then be removed by hydrogenolysis, for example using a palladium on carbon catalyst and hydrogen. The reaction is generally conducted at a temperature between about 10°–50° C., preferably at about room temperature, in an inert organic solvent, such as an ether like tetrahydrofuran, dioxane or dimethoxyethane, or an n-alkanol of 1 to 4 carbon atoms, particularly methanol or ethanol. The 1-(2-hydroxy-3-n-alkoxypropyl)-piperazine (i.e. where $R_2$ is hydrogen) formed in this manner can then be further reacted to form those compounds having other $R_2$ groups. Thus, for example, the 1-(2-hydroxy-3-n-alkoxypropyl)-piperazine may be reacted with an appropriately substituted benzyl halide in the presence of a base, for example a trialkyl amine such as triethylamine. The reaction is generally conducted in an inert organic solvent, for examle an ether such as tetrahydrofuran, dioxane, dimethoxyethane and the like, at temperatures in the range of about 50°–150° C., preferably at reflux temperature of the solvent. Compounds where $R_2$ is alkyl may be prepared by reaction of 1-(2-hydroxy-3-n-alkoxypropyl)-piperazine with an appropriate alkyl halide using the reaction conditions described above for reaction of a benzyl halide.

Preparation of the $(R_2,R_3)$-substituted-piperadino compounds of this invention wherein $R_3$ is aminomethyl is effected by reaction of the appropriate 4-$R_2$-4-cyanopiperidine with the appropriate 2,3-epoxypropyl-n-alkyl ether as described above to form the 4-cyano-1-(2-hydroxy-3-n-alkoxypropyl)-4-$R_2$-piperidine. The 4-cyano group is then readily reduced to aminomethyl, for example with Raney nickel and hydrogen. The reaction is effected at a temperature of about 40°–140° C. in an inert organic solvent such as an ether like tetrahydrofuran, dioxane, dimethoxyethane and similar solvents.

Preparation of the $(R_2,R_3)$-substituted-piperidine compounds wherein $R_3$ is a carboxamide group is effected by reaction of the appropriate 2,3-epoxypropyl-n-alkyl ether with an $R_2$-substituted-4-carboxamidopiperidine using the reaction methods described above. If desired, the 4-carboxamido-1-(2-hydroxy-3-n-alkoxypropyl)-piperidine may be employed as an intermediate for the preparation of the corresponding 4-aminomethyl-substituted compounds by reduction of the 4-carboxamido group with a metal hydride, such as lithium aluminum hydride or sodium bis(2-methoxyethoxy)aluminum hydride and the like, generally at a temperature between about 25°–100° C. in an inert organic solvent such as benzene, toluene, xylene and the like.

The pharmaceutically acceptable acid addition salts of the novel substituted piperazines and piperidines of formula I are readily prepared by contacting the free base with the appropriate mineral or organic acid in either aqueous solution or in a suitable organic solvent, for example a lower alkanol having from 1 to 6 carbon atoms. The solid salt may then be obtained by precipitation or by evaporation of the solvent. The pharmaceutically acceptable acid addition salts of this invention include, but are not limited to, the hydrochloride, hydrobromide, hydroiodide, sulfate, bisulfate, nitrate, phosphate, acetate, lactate, maleate, fumarate, oxalate, citrate, tartrate, succinate, gluconate, methanesulfonate, and the like.

The novel compounds of this invention and their pharmaceutically acceptable acid addition salts are useful regulants of the immune response in warm-blooded animals. These compounds are therefore useful in the treatment of conditions such as rheumatoid arthritis and other diseases associated with immune deficiency and accompanied by inflammation. Like the known compound Levamisole, presently a preferred compound for the treatment of rheumatoid arthritis, the compounds of the present invention act to regulate the immune response of the subject and thereby alleviate the underlying immune disorder by maintaining immune competence. In addition, the activity of the present novel compounds as immune regulants makes them useful in maintaining the immune response of a warm-blooded animal to increase the resistance of the subject to tumors, the compounds acting to stimulate the natural immune system of the subject to reject tumors.

The present invention therefore also embraces a method of immune regulation in a warm-blooded animal by administering to the subject an effective immune regulant amount of a compound of the present invention of formula I or a pharmaceutically acceptable acid addition salt thereof. In accord with this method, the compounds of the present invention may be administered to the subject in need of treatment by conventional routes, such as orally or parenterally, dosages in the range of about 0.10 to about 75 mg/kg body weight of the subject per day, preferably about 0.15 to about 15 mg/kg body weight per day being suitable. However, the optimum dosage for the individual subject being treated will be determined by the person responsible for treatment, generally smaller doses being administered initially and thereafter gradual increments made to determine the most suitable dosage. This will vary according to the particular compound employed and with the subject being treated. In this regard, the immune competence of the subject being treated may be monitored following administration using conventional techniques employed in the art and the response of the subject determined.

The compounds of this invention may be used in pharmaceutical preparations containing the compound or a pharmaceutically acceptable acid addition salt thereof in combination with a pharmaceutically acceptable carrier or diluent. Suitable pharmaceutically acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds may be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like. For parenteral administration the compounds may be combined with sterile aqueous or organic media to form injectable solutions or suspensions. For example, solutions of the compounds of formula I in sesame or peanut oil, aqueous propylene glycol and the like may be used, as well as aqueous solutions or water soluble pharmaceutically acceptable acid addition salts of the compounds. The injectable solutions prepared in this manner may then be administered intraveneously, interperitoneally, subcutaneously or intramuscularly, with intravenous and interperitoneal administration being preferred.

The immune regulant activity of the compounds of the present invention may be determined by such standard pharmacological tests as the stimulation in vitro of lymphocyte proliferation of murine thymus cells cultured in the presence of Concanavalin A (Con A) employing the general evaluation procedure of V. J. Merluzzi et al., see Journal of Clinical and Experimental Immunology, Volume 22, page 486 (1975). In this study, three different levels of peak lymphocyte stimulation assay (LSA) activity were established for the compounds undergoing evaluation, viz., those equal to Con A alone; those superior to Con A activity but less than levamisole, the standard compound of choice in this area; and those having an activity equal to levamisole. Compounds are considered to be active for the present purposes if they are superior to Concanavalin A.

The immune regulant activity of the compounds of the present invention may also be determined by an assessment of tumor rejection in, for example, the sarcoma 180 J model. In this test, the increased life span (% ILS) is determined for a group of female CD-1 mice (20–25 g). The mice receive $10^6$ S-180 J cells which are 5 to 8 days old, by intraperitoneal administration. On the day following tumor inoculation the mice receive 0.1 ml of the test compound formulated in Tween-glycerol at the desired dose level and are then observed until death or for 40 days, whichever occurs first. The increased life span is then determined from the ratio of the mean survival time of drug treated mice to the mean survival time of untreated control group mice.

The present invention is illustrated by the following examples. However, it should be understood that the invention is not limited to the specific details of these examples.

EXAMPLE 1

Allyl-n-hexadecylether:

n-Hexadecanol (24.2 g, 0.1 mol) was added to a suspension of sodium hydride (9.6 g of a 50% dispersion in mineral oil, 0.2 mol) in dimethylformamide (200 ml) and heated to 50° C. for 30 minutes. Allyl bromide, (24.2 g, 0.2 mol) was then added and the mixture heated to 90° C. for 5 hours. The reaction was cooled, diluted with a solution of saturated sodium chloride (300 ml), and extracted with ether ($2 \times 300$ ml). The combined ether extracts were washed with a saturated solution of sodium chloride (200 ml), filtered, dried over magnesium sulfate, treated with activated charcoal, filtered, and evaporated under reduced pressure to an oil. The resulting oil was purified by absorbing it on silica gel, placing the silica gel in a sintered glass filter, and eluting the product off with hexane ($7 \times 200$ ml) followed by toluene ($4 \times 200$ ml). Concentration yielded the pure ether (14 g, 50% yield): NMR (CDCl$_3$) 3.40 (t, 2, —C$\underline{H}$$_2$—O—CH$_2$CH=CH$_2$), 3.92 (d, 2, —O—C$\underline{H}_2$CH=CH$_2$), 4.95–5.38 (m, 2, =C$\underline{H}_2$) and 5.58–6.20 (m, 1, —C$\underline{H}$=CH$_2$).

EXAMPLE 2

2,3-Epoxypropyl-n-hexadecylether

Allyl-n-hexadecylether (37 g, 0.13 mol) was dissolved in methylene chloride (200 ml) and treated with m-chloro-perbenzoic acid (31 g, 0.18 mol) at room temperature for 16 hours. More m-chloroperbenzoiz acid (2.0 g, 0.01 mol) was added and the mixture stirred an additional 16 hours. The mixture was then filtered, treated with a saturated solution of sodium sulfite, and stirred for 2 hours. The methylene chloride layer was separated, washed with a saturated solution of sodium bicarbonate ($4 \times 500$ ml) and water (500 ml), dried over magnesium sulfate, filtered and concentrated under reduced pressure to the desired epoxide, which solidified on cooling (35 g, 92% yield): mp 30°–31.5° C.; NMR (CDCl$_3$) 1.3 (S, 28, aliphatic methylene), 2.55 (d of d, 1, epoxide), 2.73 (t, 1, epoxide) and 3.03 (m, 1, epoxide).

EXAMPLE 3

1-Benzyl-4-(2-hydroxy-3-n-hexadecyloxypropyl)piperazine 2,3-Epoxypropyl-n-hexadexylether (2.0 g, 0.0067 mol) and 1-benzylpiperazine (2.03 g, 0.011 mol) were combined and heated to 180° C. for 20 minutes. The resulting mixture was dissolved in acetone and cooled in a dry ice/acetone bath. The solids that formed were filtered, dissolved in ether, and treated with gaseous hydrochloric acid. The desired amine hydrochloride was obtained by concentrating the ether solution and recrystallizing the resulting solid from isopropyl alcohol (0.8 g, 13% yield): mp 237°–238° C.; NMR [(CD$_3$)$_2$SO] 1.32 (S, 28, aliphatic methylene) and 4.55 (S, 2, Ph—C$\underline{H}_2$—N).

Anal: Calcd for C$_{30}$H$_{54}$O$_2$N$_2$.2HCl.$\frac{1}{2}$ H$_2$O: C, 64.72; H, 10.32; N, 5.03. Found: C, 64.87; H, 10.22; N, 5.00.

EXAMPLE 4

1-(2-Hydroxy-3-n-hexadecyloxypropyl)-piperazine

1-Benzyl-4-(2-hydroxy-3-n-hexadecyloxypropyl)-piperazine hydrochloride (8 g, 0.0146 mol) was dissolved in toluene (100 ml), methanol (100 ml) and tetrahydrofuran (700 ml) and divided into three 300 ml portions. Each portion was hydrogenated overnight at room temperature on a Parr shaker using a 10% palladium on carbon catalyst (2 g) and 50 p.s.i.g. hydrogen. The catalyst was filtered off and the filtrate evaporated under reduced pressure to a solid, which was triturated under acetone and filtered to give a total yield of product of 2.9 g (43%), mp 230° C. (dec).

Anal: Calcd for C$_{23}$H$_{48}$O$_2$N$_2$.2HCl: C, 60.37; H, 11.01; N, 6.12. Found: C, 60.26; H, 10.71; N, 5.97.

EXAMPLE 5

1-(3,4-Dichlorobenzyl)-4-(2-hydroxy-3-n-hexadecyloxypropyl)-piperazine 1-1(2-Hydroxy-3-n-hexadecyloxypropyl)-piperazine (0.7 g, 0.0015 mol), 3,4-dichlorobenzylchloride (0.328 g, 0.00168 mol) and triethylamine (1.39 ml, 0.01 mol) were refluxed in tetrahydrofuran (50 ml) for 16 hours. The mixture was cooled, diluted with water (200 ml) and extracted with ether (200 ml). The ether extract was washed with water ($2 \times 100$ ml), dried over magnesium sulfate, filtered and concentrated under reduced pressure. The resulting oil was purified by silica gel chromatography (eluted with 5% ethanol in toluene), converted to the hydrochloride salt and recrystallized from hot isopropyl alcohol to give pure product (0.35 g, 38% yield): mp 236°–237° C.

Anal: Calcd for C$_{30}$H$_{52}$O$_2$N$_2$Cl$_2$.2HCl: C, 58.44; H, 8.83; N, 4.54. Found: C, 58.06; H, 8.90; N, 4.48.

EXAMPLE 6

1-Methyl-4-(2-hydroxy-n-hexadecyloxypropyl)-piperazine

Following the procedures of Example 3, 2,3-epoxypropyl-n-hexadecylether was reacted with 1-methylpiperazine to form 1-methyl-4-(2-hydroxy-n-hexadecyloxypropyl)piperazine, mp 209–211° C.

Anal: Calcd for $C_{24}H_{50}O_2N_2.2HCl.\frac{1}{2}H_2O$: C, 59.98; H, 11.12; N, 5.82. Found: C, 59.80; H, 10.88; N, 5.70.

EXAMPLE 7

1-Benzyl-4-(2-hydroxy-3-n-octadecyloxypropyl)-piperazine

Following the procedure of Examples 1 to 3, 2,3-epoxypropyl-n-octadecylether and 1-benzylpiperazine were reacted to form 1-benzyl-4-(2-hydroxy-3-n-octadecyloxypropyl)-piperazine, mp 235°–236° C.

Anal: Calcd for $C_{32}H_{58}O_2N_2.2HCl/3/4H_2O$: C, 65.23; H, 10.52; N, 4.75. Found: C, 65.39; H, 10.26; N, 4.75.

EXAMPLE 8

1-(4-Chlorobenzyl)-4-(2-hydroxy-3-n-hexadecyloxypropyl)piperazine

Following the procedure of Example 5, 1-(2-hydroxy-3-n-hexadecyloxypropyl)-piperazine was reacted with 4-chlorobenzylchloride to form 1-(4-chlorobenzyl)-4-(2-hydroxy-3-n-hexadecyloxypropyl)-piperazine, mp 237°–239° C.

Anal: Calcd for $C_{30}H_{53}O_2N_2Cl.2-HC.1/4H_2O$: C, 61.42; H, 9.53; N, 4.78. Found: C, 61.39; H, 9.10; N, 4.75.

EXAMPLE 9

1-(4-Methylbenzyl)-4-(2-hydroxy-3-n-hexadecyloxypropyl)piperazine

Following the procedure of Example 5, 1-(2-hydroxy-3-n-hexadecyloxypropyl)-piperazine was reacted with 4-methylbenzyl chloride to form 1-(4-methylbenzyl)-4-(2-hydroxy-3-n-hexadecyloxypropyl)-piperazine, mp 238°–239° C.

Anal: Calcd for $C_{31}H_{56}O_2N_2.2HCl/3/4HCl$: C, 64.73; H, 10.42; N, 4.87. Found: C, 64.75; H, 10.36; N, 4.96.

EXAMPLE 10

1-(3-Trifluoromethylbenzyl)-4-(2-hydroxy-3-n-hexadecyloxypropyl)-piperazine

Following the procedure of Example 5, 1-(2-hydroxy-3-n-hexadecyloxypropyl)-piperazine was reacted with 3-(trifluoromethyl)benzyl chloride to form 1-(3-trifluoromethylbenzyl)-4-(2-hydroxy-3-n-hexadecyloxypropyl)piperazine, mp 133°–135° C.

Anal: Calcd for $C_{30}H_{51}O_2N_2F_3.HCl$: C, 63.75; H, 9.27; N, 4.96. Found: C, 63.62; H, 9.13; N, 4.87.

EXAMPLE 11

1-(4-Fluorobenzyl)-4-(2-hydroxy-3-n-hexadecyloxypropyl)piperazine

Following the procedure of Example 5, 1-(2-hydroxy-3-n-hexadecyloxypropyl)-piperizine was reacted with 4-fluorobenzyl chloride to form 1-(4-fluorobenzyl)-4-(2-hydroxy-3-n-hexadecyloxypropyl)-piperazine, mp 242° C. (dec).

Anal: Calcd for $C_{30}H_{53}O_2N_2F.2HCl.1/4H_2O$: C, 63.20; H, 9.81; N, 4.91.

EXAMPLE 12

1-(4-Methoxybenzyl)-4-(2-hydroxy-3-n-hexadecyloxypropyl)piperazine

Following the procedure of Example 5, 1-(2-hydroxy-3-n-hexadecyloxypropyl)-piperazine was reacted with 4-methoxybenzyl chloride to form 1-(4-methoxybenzyl)-4-(2-hydroxy-3-n-hexadecyloxypropyl)-piperazine, mp 233°–245° C.

Anal: Calcd for $C_{31}H_{56}O_3N_2.2HCl.1/4H_2O$: C, 63.95; H, 10.13; N, 4.81. Found: C, 63.74; H, 9.88; N, 4.78.

EXAMPLE 13

1-Benzyl-4-(2-hydroxy-3-n-dodecyloxypropyl)-piperazine

Following the procedures of Examples 1 to 3, 2,3-epoxypropyl-n-dodecylether and 1-benzylpiperazine were reacted to form 1-benzyl-4-(2-hydroxy-3-n-dodecyloxypropyl)-piperazine, mp 239°–239° C. (dec).

Anal: Calcd for $C_{26}H_{46}O_2N_2.2HCl$: C, 63.53; H, 9.84; N, 5.70. Found: C, 63.88; H, 9.23; N, 5.63.

EXAMPLE 14

1-(4-Fluorobenzyl)-4-(2-hydroxy-3-n-dodecyloxypropyl)piperazine

Following the procedures of Examples 4 and 5, 1-benzyl-4-(2-hydroxy-3-n-dodecyloxypropyl)-piperazine was converted to 1-(2-hydroxy-3-n-dodecyloxypropyl)-piperazine by hydrogenolysis using a palladium on carbon catalyst. The hydrogenolysis product was reacted with 4-fluorobenzyl chloride to form 1-(4-fluorobenzyl)-4-(2-hydroxy-3-n-dodecyloxypropyl)-piperazine, mp 243°–245° C.

Anal: Calcd for $C_{26}H_{45}O_2N_2F.2HCl.H_2O$: C, 59.19; H, 9.36; N, 5.31. Found: C, 59.35; H, 9.25; N, 5.79.

EXAMPLE 15

1-Phenyl-4-(2-hydroxy-3-n-hexadecyloxypropyl)-piperazine

Following the procedure of Example 3, 2,3-epoxypropyl-n-hexadecylether and 1-phenylpiperazine were reacted to form 1-phenyl-4-(2-hydroxy-3-n-hexadecyloxypropyl)-piperazine, mp 195°–196° C.

Anal: Calcd for $C_{29}H_{52}O_2N_2.2HCl$: C, 65.27; H, 10.20; N, 5.25. Found: C, 65.58; H, 9.99; N, 5.45.

EXAMPLE 16

1-Benzyl-4-(2-hydroxy-3-benzyloxypropyl)-piperazine

Following the procedure of Example 3, 2,3-epoxypropylbenzyl ether and 1-benzylpiperazine were reacted to form the title compound; mp 215°–216° C.

Anal: Calcd for $C_{21}H_{28}O_2N_2.2HCl$: C, 61.02; H, 7.31; N, 6.78. Found: C, 60.48; H, 7.20; N, 6.75.

EXAMPLE 17

4-Cyano-1-(2-hydroxy-3-n-hexadecyloxypropyl)-4-phenylpiperidine

4-Cyano-4-phenylpiperidine (1.1 g, 0.0059 mol) and 2,3-epoxypropyl-n-hexadecylether (1.6 g, 0.0056 mol) were combined and heated to 185° C. for 30 minutes. After cooling, ethyl acetate (20 ml) and acetonitrile (20 ml) were added, and the resulting solid was collected by filtration (1.6 g, 62% yield): mp 69°–70° C.; ir (KBr) 2227 cm$^{-1}$.

EXAMPLE 18

4-Aminomethyl-1-(2-hydroxy-3-n-hexadecyloxypropyl)-4-phenylpiperidine hydrochloride 4-Cyano-1-(2-hydroxy-3-n-hexadecyloxypropyl)-4-phenylpiperidine (1.5 g, 0.003 mol) was dissolved in a mixture of tetrahydrofuran (50 ml) and ethanol (3 ml) saturated with ammonia. Raney-nickel (0.8 g) was added, and the mixture was hydrogenated at 50 psi (H$_2$) for 2 hours. The mixture was then filtered and concentrated under reduced pressure to a waxy solid. This solid was dissolved in methylene chloride, treated with gaseous hydrochloric acid and again concentrated to a solid. The pure product was obtained by recrystallization from isopropyl alcohol (1.0 g, 59% yield): mp 227°–228° C.

Anal. Calcd for $C_{31}H_{56}O_2N_2.2HCl$: C, 66.29; H, 10.41; N, 4.99. Found: C, 66.18; H, 10.40; N, 5.18.

EXAMPLE 19

4-Aminomethyl-1-(2-hydroxy-3-n-octadecyloxypropyl)-4-phenylpiperidine

Following the procedure of Example 17 and 18, 4-cyano-4-phenylpiperidine was reacted with 2,3-epoxypropyl-octadecylether and reduced to form 4-aminomethyl-1-(2-hydroxy-3-n-octadecyloxypropyl)-4-phenylpiperidine, mp 223°–224° C.

Anal: Calcd for $C_{33}H_{60}O_2N_2.2HCl.2.25H_2O$: C, 62.88; H, 10.63; N, 4.44. Found: C, 62.96; H, 10.25; N, 4.56.

EXAMPLE 20

4-Carboxamido-1-(2-hydroxy-3-n-hexadecyloxypropyl)piperidine

Isonipectoinamide (0.7 g, 0.0055 mol) and 2,3-epoxypropyl-n-hexadecylether (1.49 g, 0.005 mol) were combined and heated to 180° C. for 20 minutes. The reaction mixture was cooled, ethyl acetate (20 ml) added, and the resulting solids isolated by filtration. Recrystallization from hot ethyl acetate (15 ml) gave pure product (1.6 g, 75% yield): mp 97°–98° C.; ir (KBr) 1653 cm$^{-1}$.

Anal: Calcd for $C_{25}H_{50}O_3N_2$: C, 70.37; H, 11.81; N, 6.57. Found: C, 69.90; H, 11.42; N, 6.50.

EXAMPLE 21

4-Aminomethyl-1-(2-hydroxy-3-n-hexadecyloxypropyl)piperidine hydrochloride

4-Carboxamido-1-(2-hydroxy-3-n-hexadecyloxypropyl)piperidine (1.1 g, 0.0026 mol) was dissolved in toluene (20 ml) and a 70% solution of sodium bis-(2-methoxyethoxy)aluminum hydride (3.5 ml) was slowly added over 15 minutes. The reaction mixture was heated to 80° C. for 16 hours and worked up by dropwise addition of ethyl acetate (10 ml) and then water (20 ml), followed by extraction with ether (50 ml). The ether extract was washed with water (2×50 ml), dried over magnesium sulfate, filtered, converted to the hydrochloride salt, and concentrated to a solid under reduced pressure. Pure product (0.25 g, 20% yield) was obtained by recrystallization from hot isopropyl alcohol/acetone (1/1): mp 202° C. (dec).

Anal: Calcd for $C_{25}H_{52}O_2N_2.2HCl.3/4H_2O$: C, 60.16; H, 11.20; N, 5.61. Found: C, 60.23; H, 10.53; N, 5.55.

EXAMPLE 22

1-(2-Hydroxy-3-n-hexadecyloxypropyl)-4-phenylpiperidine

4-Phenylpiperidine (1.8 g, 0.011 mol) and 2,3-epoxypropyl-n-hexadecylether (2.98 g, 0.01 mol) were combined and heated to 180° C. for 30 minutes. The reaction mixture was cooled, acetone was added, and the mixture was stirred for 16 hours. The resulting solids were collected and recrystallized from hot acetone to give pure product (2.3 g, 50% yield): mp 64°–65° C.

Anal: Calcd for $C_{30}H_{53}O_2N$: C, 78.37; H, 11.62; N, 3.05. Found: C, 78.64; H, 11.42; N, 3.26.

EXAMPLE 23

1-(2-Hydroxy-3-n-octadecyloxypropyl)-4-phenylpiperidine:

Following the procedure of Example 22, 2,3-epoxypropyl-n-octadecylether was reacted with 4-phenylpiperidine to give 1-(2-hydroxy-3-n-octadecyloxypropyl)-4-phenylpiperidine, mp 170°–171° C.

Anal: Calcd for $C_{32}H_{57}O_2N.HCl$: C, 73.31; H, 11.15; N, 2.67. Found: C, 73.57; H, 10.95; N, 2.54.

EXAMPLE 24

4-Methyl-1-(2-hydroxy-3-n-hexadecyloxypropyl)-piperidine

Following the procedure of Example 22, 2,3-epoxypropyl-n-hexadecylether was reacted with 4-methylpiperidine to form 4-methyl-1-(2-hydroxy-3-n-hexadecyloxypropyl)-piperidine, mp 84°–85° C.

Anal: Calcd for $C_{25}H_{51}O_2N.HCl.1/4H_2O$: C, 68.45; H, 12.06; N, 3.19. Found: C, 68.58; H, 12.28; N, 3.09.

EXAMPLE 25

Sarcoma 180J Model for Assessment of Tumor Rejection:

Six female CD-1 mice (20–25 g) per group received $10^6$ S-180J cells which were 5 to 8 days old by intraperitoneal administration. On the day following tumor innoculation the mice received 0.1 ml of the test compound formulated in the fat emulsion vehicle Intralipid (Cutter Laboratories) by dissolving the drug in a minimum amount of alcohol and adding this solution to the Intralipid at the desired dose and were then observed until death or 40 days, whichever occurs first. Results are expressed as increased percent life span (%ILS), defined as follows:

%ILS = (S − Sc)/Sc × 100

Where
S = Mean Survival time of Drug Treated Mice; and
Sc = Mean Survival time of Control Mice.
Results obtained by the above test procedure were as follows:

| Example | % ILS | Dose (mg/kg) |
| --- | --- | --- |
| 3 | 64 | 1 |
| 4 | 73 | 15 |
| 6 | 54 | 64 |
| 10 | 28 | 15 |
| 11 | 25 | 75 |
| 13 | 89 | 75 |
| 14 | 26 | 0.6 |
| 16 | 27 | 15 |
| 18 | 78 | 16 |
| 19 | 88 | 15 |
| 20 | 115 | 16 |

EXAMPLE 26

The immune regulant activity of the compounds of Examples 3, 5, 7, 9, 11, 13, 14, 15 and 16 was evaluated by determining their ability to stimulate, in vitro the lymphocyte proliferation of murine thymus cells cultured in the presence of Concanavalin A (Con A) by employing the procedure of V. J. Merluzzi et. al., as essentially described in the *Journal of Clinical and Experimental Immunology*, Vol. 22, p. 486 (1975). The cells were derived from male C57B1/6 mice of from 6-8 weeks age, purchased from the Jackson Laboratories of Bar Harbor, Maine and the Con A was obtained from Sigma Chemicals of St. Louis, Missouri. Each cell culture (consisting of 0.10 ml thymus cells stock solution, 0.05 ml of Con A stock solution and 0.05 ml of drug solution) was performed in quadruplicate and cellular proliferation was measured, after 48 hours of incubation at 37° C., by pulsing each culture with $^3$H-thymidine (0.01 ml of specific activity 1.9 C/mM, obtained from Schwarz-Mann, Inc. of Orangeburg, N.Y.) and then determining the incorporation of $^3$H-thymidine into cellular desoxyribonucleic acid (DNA) by an assessment of radioactivity using a liquid scintillation counter. The results obtained in this manner are expressed quantitatively in terms of the average counts per minute (cpm) of $^3$H-thymidine incorporated at each drug level. On this bases, three different levels of peack activity were established in the present lymphocyte stimulation assay (LSA) and these are defined in the manner hereinafter indicated, viz., those levels equal to Con A alone (6,000±300 cpm) were assigned a negative value or score of zero; those superior (10,000±700 cpm) to Con A activity but less than levamisole were scored as +; while those equal to levamisole (30,000±900 cpm) were scored as ++ Minimum effective concentrations (MEC) were determined at activity levels with a score of +.

| Example | Peak Activity Activity Level | Drug Concentration (μg/ml) |
|---|---|---|
| 3 | + | 0.10 |
| 5 | + | 1.0 |
| 7 | + | 0.01 |
| 9 | + | 0.01 |
| 11 | + | 0.30 |
| 13 | + | 0.30 |
| 14 | + | 0.10 |
| 15 | + | 0.30 |
| 16 | ++ | 0.04 |
| Levamisole | ++ | 28 |

| Potency at + Activity Level | |
|---|---|
| Example | MEC (μg/ml) |
| 3 | 0.004 |
| 5 | 0.10 |
| 7 | <0.004 |
| 9 | <0.004 |
| 11 | 0.04 |
| 13 | <0.004 |
| 14 | 0.10 |
| 15 | 0.004 |
| 16 | <<0.004 |
| Levamisole | 1.0 |

I claim:

1. A compound of the formula

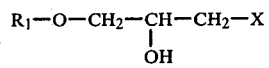

and the pharmaceutically acceptable acid addition salts thereof, wherein $R_1$ is n-alkyl of 10 to 20 carbon atoms; and X is

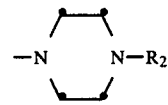

wherein $R_2$ is selected from the group consisting of hydrogen, alkyl of 1 to 3 carbon atoms, benzyl, monosubstituted benzyl, phenyl and monosubstituted phenyl, wherein said substituents are selected from the group consisting of chloro, bromo, fluoro, alkyl of 1 to 3 carbon atoms and alkoxy of 1 to 3 carbon atoms.

2. A compound of claim 1 wherein $R_1$ is n-alkyl of 16 to 20 carbon atoms.

3. A compound of claim 1 whrein $R_2$ is benzyl or monosubstituted benzyl.

4. A compound of claim 3 wherein $R_1$ is n-alkyl of 16 carbon atoms.

5. A compound of claim 4 wherein $R_2$ is benzyl.

6. A compound of claim 4 wherein $R_2$ is 4-chlorobenzyl.

7. A compound of claim 4 wherein $R_2$ is 4-methylbenzyl.

8. A compound of claim 4 wherein $R_2$ is 4-fluorobenzyl.

9. A compound of claim 4 wherein $R_2$ is 4-methoxybenzyl.

10. A compound of claim 3 wherein $R_2$ is benzyl and $R_1$ is n-alkyl of 18 carbon atoms.

11. A compound of claim 1 wherein $R_2$ is phenyl or monosubstituted phenyl.

12. A compound of claim 11 wherein $R_2$ is phenyl and $R_1$ is n-alkyl of 16 carbon atoms.

13. A compound of claim 1 wherein $R_2$ is hydrogen and $R_1$ is n-alkyl of 16 carbon atoms.

14. A pharmaceutical composition comprising an immuneregulant effective amount of a compound of claim 1 and a pharmaceutically acceptable carrier.

15. A composition of claim 14 wherein $R_2$ is benzyl or monosubstituted benzyl.

16. A composition of claim 15 wherein $R_2$ is benzyl and $R_1$ is n-alkyl of 16 carbon atoms.

17. A composition of claim 14 wherein $R_2$ is hydrogen and $R_1$ is n-alkyl of 16 carbon atoms.

18. A method of immune regulation in a host which comprises administering to said host an effective immune regulant amount of a compound of claim 1.

19. A method of claim 18 wherein $R_2$ is benzyl or monosubstituted benzyl.

20. A method of claim 19 wherein $R_2$ is benzyl and $R_1$ is n-alkyl of 16 carbon atoms.

21. A method of claim 18 wherein $R_2$ is hydrogen and $R_1$ is n-alkyl of 16 carbon atoms.

* * * * *